United States Patent
Aoki et al.

(10) Patent No.: US 12,207,964 B2
(45) Date of Patent: Jan. 28, 2025

(54) RADIATION DETECTION APPARATUS

(71) Applicant: CANON KABUSHIKI KAISHA, Tokyo (JP)

(72) Inventors: Makoto Aoki, Tokyo (JP); Tomohisa Ishigami, Tokyo (JP); Hajime Shimura, Kanagawa (JP); Tomoyasu Soma, Kanagawa (JP); Yutaka Ishinari, Kanagawa (JP); Hiroto Kondo, Tokyo (JP); Motoki Tagawa, Kanagawa (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 190 days.

(21) Appl. No.: 18/057,562

(22) Filed: Nov. 21, 2022

(65) Prior Publication Data

US 2023/0181145 A1 Jun. 15, 2023

(30) Foreign Application Priority Data

Dec. 9, 2021 (JP) ................. 2021-200400

(51) Int. Cl.
*G01T 1/172* (2006.01)
*A61B 6/00* (2006.01)
(Continued)

(52) U.S. Cl.
CPC .............. *A61B 6/56* (2013.01); *A61B 6/4208* (2013.01); *G01T 1/2018* (2013.01)

(58) Field of Classification Search
CPC ....... A61B 6/4208; A61B 6/42; A61B 6/4283; A61B 6/4429; A61B 6/4405;
(Continued)

(56) References Cited

U.S. PATENT DOCUMENTS 9,716,319 B2 7/2017 Caratelli
10,061,042 B2 8/2018 Suzuki
(Continued)

FOREIGN PATENT DOCUMENTS

JP 2010-118845 A 5/2010
JP 2011-112923 A 6/2011
(Continued)

OTHER PUBLICATIONS

Hirasawa, Kazuhiro, "Antenna characteristics and basic technology for solutions," The Nikkan Kogyo Shimbun, Ltd. (Feb. 17, 2011) 113-39.

(Continued)

*Primary Examiner* — Don K Wong
(74) *Attorney, Agent, or Firm* — VENABLE LLP (57) ABSTRACT

A radiation detection apparatus includes a housing having an incident face and a side face, a reflective member accommodated within the housing, the reflective member having a reflective face which reflects radio waves, and an antenna element accommodated within the housing. The side face of the housing includes a conductor region and a transmissive region, the transmissive region having a higher radio wave transmittance than the conductor region. The reflective member is disposed in a position at which a first radio wave, which proceeds directly from the antenna element toward the transmissive region, and a second radio wave, which reaches the reflective face from the antenna element and is reflected toward the transmissive region by the reflective face, strengthen each other.

16 Claims, 9 Drawing Sheets

(51) Int. Cl.
*A61B 6/42* (2024.01)
*G01T 1/20* (2006.01)

(58) Field of Classification Search
CPC ..... A61B 6/4411; A61B 6/4233; A61B 6/425;
A61B 6/4266; A61B 6/56; A61B 6/563;
A61B 5/0002; A61B 2562/0228; A61B
2562/04; A61B 2562/06; A61B 2562/16;
G01T 7/00; G01T 1/20184; G01T 1/247
See application file for complete search history.

(56) References Cited

U.S. PATENT DOCUMENTS

| | | | |
|---|---|---|---|
| 10,156,641 | B2 | 12/2018 | Hiratsuka |
| 10,651,562 | B2 | 5/2020 | Kosaka |
| 10,721,839 | B2 | 7/2020 | Tagawa |
| 11,047,995 | B2 | 6/2021 | Yagi |
| 11,128,820 | B2 | 9/2021 | Tamura |
| 11,224,390 | B2 | 1/2022 | Tagawa |
| 11,320,546 | B2 | 5/2022 | Kondo |
| 2010/0119234 | A1 | 5/2010 | Suematsu |
| 2012/0228499 | A1 | 9/2012 | Koyanagi |
| 2013/0129048 | A1 | 5/2013 | Chicchetti |
| 2014/0239189 | A1* | 8/2014 | Sakino .................. H04N 25/75 250/394 |
| 2015/0236428 | A1 | 8/2015 | Caratelli |
| 2019/0036225 | A1 | 1/2019 | Kosaka |
| 2019/0058242 | A1 | 2/2019 | Tabe |
| 2020/0106181 | A1 | 4/2020 | Avser |
| 2020/0251806 | A1 | 8/2020 | Roy |
| 2020/0348427 | A1 | 11/2020 | Kondo |
| 2021/0011176 | A1 | 1/2021 | Ishinari |
| 2022/0196859 | A1 | 6/2022 | Fujiyoshi |
| 2022/0247927 | A1 | 8/2022 | Kida |

FOREIGN PATENT DOCUMENTS

| | | |
|---|---|---|
| JP | 2015-533046 A | 11/2015 |
| JP | 2019-122831 A | 7/2019 |
| JP | 2019-164069 A | 9/2019 |
| WO | 2017/141856 A | 8/2017 |

OTHER PUBLICATIONS

U.S. Appl. No. 18/054,267, Hajime Shimura, filed Nov. 10, 2022.

* cited by examiner

RADIATION DETECTION APPARATUS

BACKGROUND OF THE INVENTION

Field of the Invention

The present invention relates to a radiation detection apparatus.

Description of the Related Art

Many digital radiography apparatuses have been commercialized as thin, lightweight, portable radiography apparatuses. Japanese Patent Laid-Open No. 2011-112923 proposes a wireless radiography apparatus that communicates wirelessly with an external apparatus to improve portability. In this radiation imaging apparatus, to efficiently propagate radio waves to the outside of the apparatus from an antenna inside the housing which is constituted by a conductive material, part of the housing is replaced with a non-conductive cover. Increasing the radio emission amount at the operating frequency by increasing the strength of the data signal for wireless communication is discussed in HIRASAWA, Kazuhiro, "Antenna characteristics and basic technology for solutions," The Nikkan Kogyo Shimbun, Ltd., Feb. 17, 2011, pp. 113-139.

SUMMARY OF THE INVENTION

In a radiation detection apparatus capable of wireless communication, it is desirable to efficiently propagate radio waves from an antenna within the housing to the outside of the housing, in order to conserve power, for example. An aspect of the present disclosure provides a technique for efficiently propagating radio waves from an antenna within a housing to the outside of the housing.

In some embodiments, a radiation detection apparatus is provided. The apparatus comprises a housing having an incident face and a side face, a reflective member accommodated within the housing, the reflective member having a reflective face which reflects radio waves, and an antenna element accommodated within the housing. The side face of the housing includes a conductor region and a transmissive region, the transmissive region having a higher radio wave transmittance than the conductor region. The reflective member is disposed in a position at which a first radio wave, which proceeds directly from the antenna element toward the transmissive region, and a second radio wave, which reaches the reflective face from the antenna element and is reflected toward the transmissive region by the reflective face, strengthen each other.

The antenna element and the transmissive region may be positioned in a normal direction of the reflective face of the reflective member.

A distance between the antenna element and the reflective face in the normal direction of the reflective face may be greater than $\lambda/8$ and less than $3\lambda/8$, $\lambda$ representing a wavelength of an operating frequency of the antenna element.

A length of the reflective face in a direction parallel to the incident face may be greater than $n\lambda/2-\lambda/8$ and less than $n\lambda/2+\lambda/8$, n representing an integer and $\lambda$ representing a wavelength of an operating frequency of the antenna element.

In plan view relative to the transmissive region, a distance between a center of the transmissive region in a direction parallel to the incident face and a center of the reflective face may be less than $\lambda/2$.

A distance between the antenna element and the reflective face in the normal direction of the reflective face may be equal to $\lambda/4$.

A length of the reflective face in a direction parallel to the incident face may be equal to $\lambda$.

A length of the reflective member in the normal direction of the reflective face of the reflective member may be greater than a skin depth of the reflective member with respect to an operating frequency of the antenna element.

The reflective face may have a concave shape.

The reflective member may be separated into a plurality of parts, and a distance between two adjacent parts among the plurality of parts may be less than $\lambda/2$.

The radiation detection apparatus may further comprise a sensor panel configured to convert radiation entering from the incident face into an electrical signal. The housing may further include a rear face on a side opposite from the incident face. The antenna element may be positioned between the sensor panel and the rear face.

The radiation detection apparatus may further comprise a support plate including a first face to which the sensor panel is mounted and a second face to which the reflective member is mounted, and a conductive member mounted to the second face of the support plate. A distance between the conductive member and the reflective face of the reflective member may be less than $\lambda/2$.

The radiation detection apparatus may further comprise a circuit board, mounted to the second face of the support plate, for operating the sensor panel. In plan view relative to the second face, the circuit board may be provided on a side of the second face that faces the antenna element.

An operating frequency of the antenna element may be within a 2.4 GHz band or a 5 GHz band.

The antenna element may be configured to wirelessly transmit an image signal generated by the radiation detection apparatus to outside the radiation detection apparatus.

Further features of the present invention will become apparent from the following description of exemplary embodiments with reference to the attached drawings.

DESCRIPTION OF THE EMBODIMENTS

Hereinafter, embodiments are described in detail with reference to the attached drawings. Note, the following embodiments are not intended to limit the scope of the claimed invention. Multiple features are described in the embodiments, but limitation is not made to an invention that requires all such features, and multiple such features may be combined as appropriate. Furthermore, in the attached drawings, the same reference numerals are given to the same or similar configurations, and redundant description thereof is omitted.

Figure 1A:
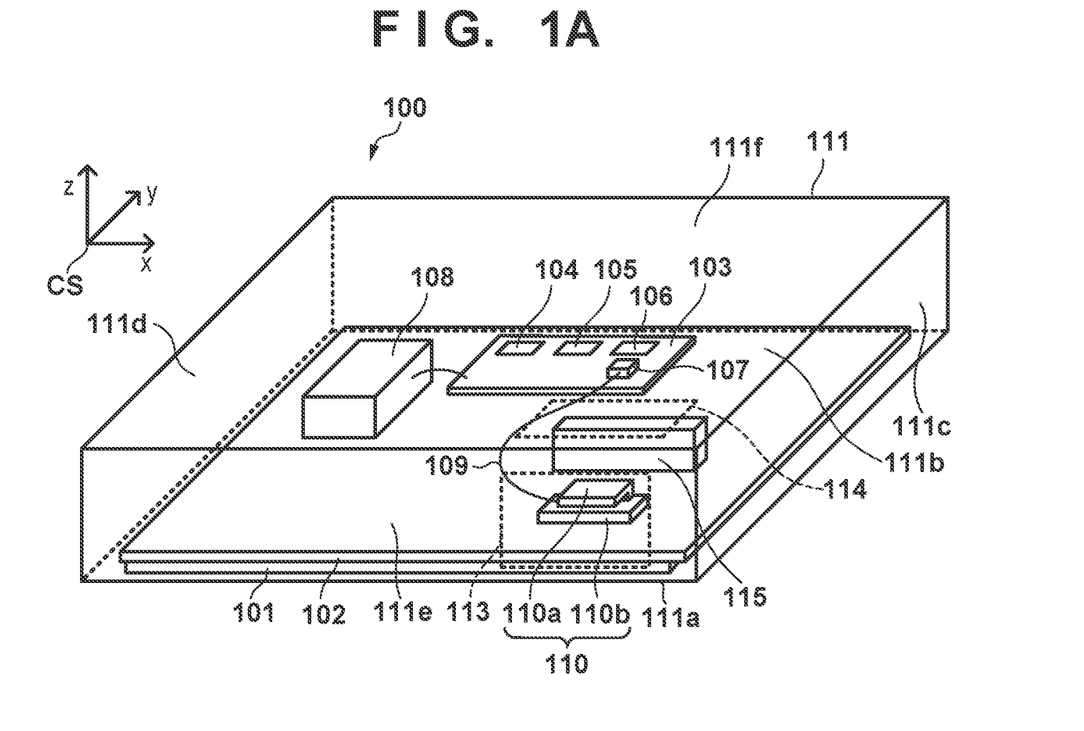
FIGS. 1A to 1C are schematic diagrams illustrating an example configuration of a radiation detection apparatus according to some embodiments.
Figure 1B:
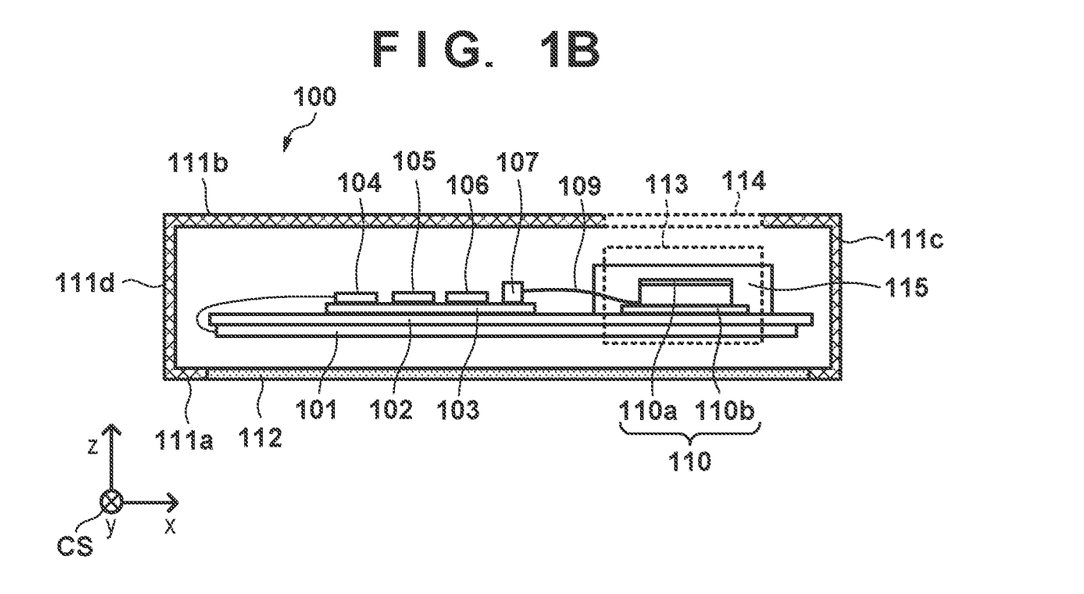
Figure 1C:
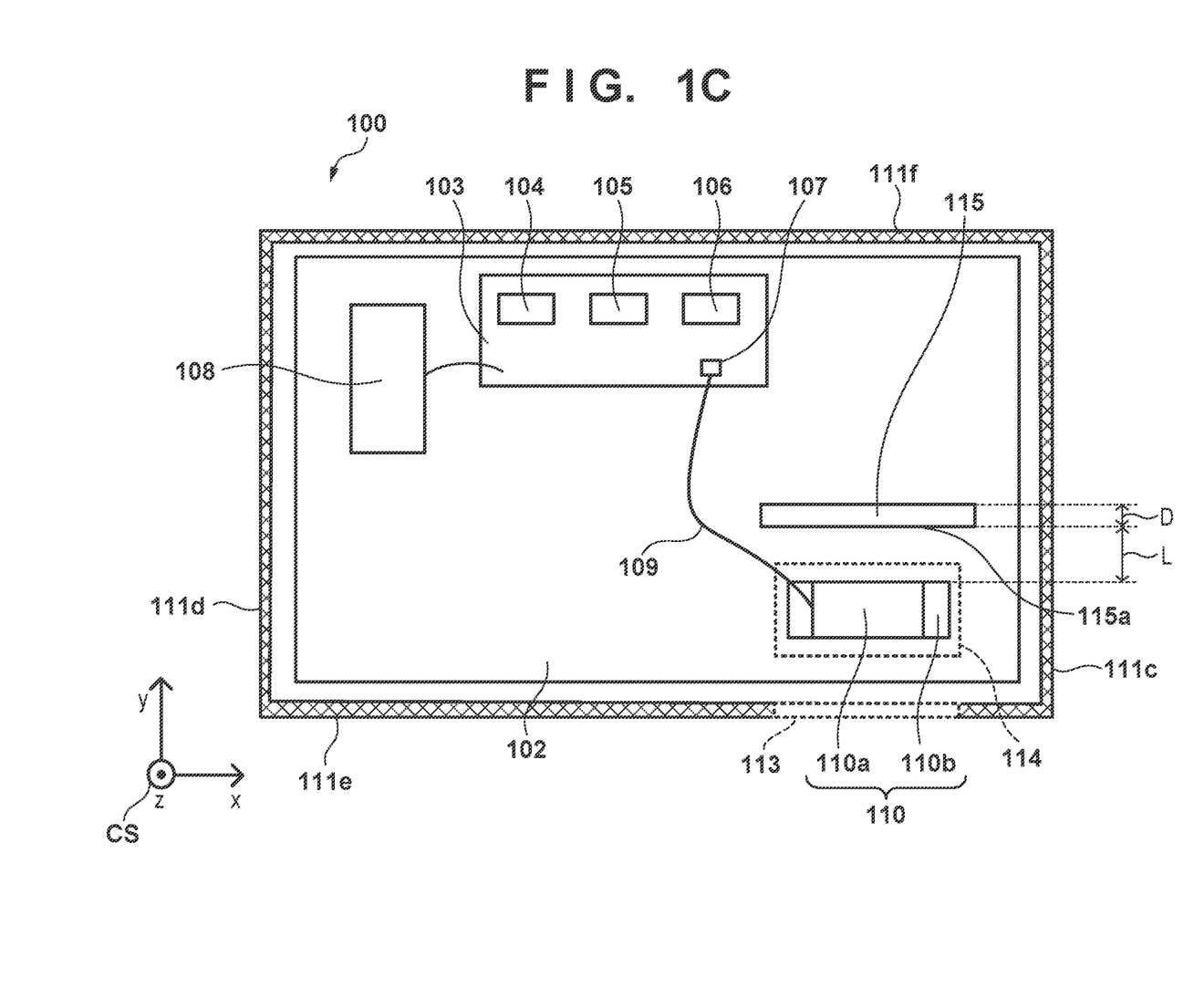

An example configuration of a radiation detection apparatus 100 according to some embodiments is described with reference to FIGS. 1A to 1C. The radiation detection apparatus 100 has a function for detecting incident radiation. When the radiation detection apparatus 100 is used to generate a radiation image, the radiation detection apparatus 100 may be referred to as a radiation imaging apparatus. FIG. 1A is a perspective view of the radiation detection apparatus 100. In FIG. 1A, a housing 111 is illustrated only as an outline so that the internal structure of the housing 111 is visible. However, the housing 111 may be formed from an opaque material. FIG. 1B is a cross-sectional side view of the radiation detection apparatus 100. FIG. 1C is a cross-sectional top view of the radiation detection apparatus 100. A three-dimensional orthogonal coordinate system CS is provided to indicate the directions of the radiation detection apparatus 100. In the following descriptions, references to an x-axis, a y-axis, and a z-axis correspond to axes in the orthogonal coordinate system CS.

The radiation detection apparatus 100 includes, for example, a sensor panel 101, a sensor support plate 102, a printed circuit board 103, a battery 108, a coaxial cable 109, an antenna 110, the housing 111, and a reflective member 115. The sensor panel 101, the sensor support plate 102, the printed circuit board 103, the battery 108, the coaxial cable 109, the antenna 110, and the reflective member 115 are contained within the housing 111. The housing 111 defines the external appearance of the radiation detection apparatus 100.

The housing 111 may have a thin, rectangular shape. A rectangle being "thin" may mean, for example, that the length of the smallest of three sides meeting at one vertex is sufficiently smaller (e.g., less than one-tenth or one-fifth) of the length of each of the other two sides. The housing 111 having a "rectangular shape" means that the housing 111 has a rectangular or similar shape. For example, the six faces of the housing 111 may be flat, stepped (including convex or concave), or curved. In any of these cases, the housing 111 is said to have a rectangular shape. Because the housing 111 defines the external appearance of the radiation detection apparatus 100, the radiation detection apparatus 100 also has a thin, rectangular shape.

Of the six faces of the housing 111, the face that faces a radiation source when the radiation detection apparatus 100 is in use is called an "incident face 111a". In the example in FIG. 1A, the bottom face of the housing 111 is the incident face 111a. In other words, radiation is emitted to the radiation detection apparatus 100 from the bottom side in FIG. 1A. Radiation irradiated from the radiation source and transmitted through a subject enters the incident face 111a and reaches the interior of the radiation detection apparatus 100 (and specifically, the sensor panel 101). Of the six faces of the housing 111, the face on the side opposite from the incident face 111a is called a "rear face 111b". Both the incident face 111a and the rear face 111b are parallel to the x-y plane.

Of the six faces of the housing 111, the four faces other than the incident face 111a and the rear face 111b are called "side faces 111c to 111f". The side face 111c and the side face 111d are opposite each other, and both are parallel to the y-z plane. The side face 111e and the side face 111f are opposite each other, and both are parallel to the x-z plane.

The housing 111 is formed from a rigid material, except in regions which are described below. This material may be a conductive material. For example, the housing 111 may be formed from a metal such as magnesium, stainless steel, aluminum, copper, iron, or the like. The housing 111 may be formed from a resin with metal embedded therein in a mesh-like pattern. The housing 111 may be formed from a conductive resin such as carbon-fiber-reinforced plastic (CFRP). A part of the incident face 111a (e.g., a part 112 overlapping the sensor panel 101 in plan view (the z-axis direction) relative to the incident face 111a) may be formed from a material having a higher radiation transmittance than the periphery thereof. The housing 111 may have a radio wave transmission region 113 in a part of the side face 111e and a radio wave transmission region 114 in a part of the rear face 111b. The radio wave transmission regions 113 and 114 are described in greater detail later.

The sensor panel 101 converts radiation entering the radiation detection apparatus 100 from the incident face 111a into an electrical signal. The sensor panel 101 has a plurality of pixel circuits arranged two-dimensionally. Each pixel circuit has a conversion element for converting radiation into a charge and a switch element for transferring electrical signals according to the amount of charge. The sensor panel 101 is mounted within the housing 111 so as to be substantially parallel to the incident face 111a. Two planes being "substantially parallel" includes not only when the two planes are parallel (i.e., the angle between the normal lines of the two planes is 0 degrees), but also when the two planes are nearly parallel (e.g., the angle between the normal lines of the two planes is less than 5 or 10 degrees).

The sensor panel 101 is supported by the sensor support plate 102. The sensor support plate 102 is mounted within the housing 111 so as to be substantially parallel to the incident face 111a. The sensor support plate 102 is also substantially parallel to the sensor panel 101. For example, the sensor support plate 102 may be mounted to the housing 111. The sensor support plate 102 may be formed from a conductive material. For example, similar to the housing 111, the sensor support plate 102 may be formed from a metal, a resin having metal embedded therein in a mesh-like pattern, or a conductive resin such as CFRP. When the sensor support plate 102 is conductive, the sensor support plate 102 may be called a "conductive plate".

The sensor panel 101 may be mounted directly to the sensor support plate 102 (i.e., the sensor panel 101 may contact the sensor support plate 102). Alternatively, a radiation shield (not shown) may be disposed between the sensor panel 101 and the sensor support plate 102. The radiation shield can protect the circuitry of the printed circuit board 103 from radiation entering the radiation detection apparatus 100 and suppress image degradation due to radiation backscatter. The sensor support plate 102 is located on the opposite side of the sensor panel 101 from the incident face 111a. In other words, the sensor support plate 102 is located between the sensor panel 101 and the rear face 111b. In plan view relative to the incident face 111a, the sensor support plate 102 may be larger than the sensor panel 101, the same size, or smaller than the sensor panel 101.

The printed circuit board 103, the battery 108, the antenna 110, and the reflective member 115 are mounted to the sensor support plate 102 (and more specifically, to the face on the side of the rear face 111b). The printed circuit board 103 contains various circuits and components for implementing the operations of the radiation detection apparatus 100. For example, the printed circuit board 103 is provided with a readout circuit 104, a control circuit 105, a wireless communication circuit 106, and a connector 107. The readout circuit 104, the control circuit 105, and the wireless communication circuit 106 may each be an integrated circuit (IC). The readout circuit 104 is configured to read out electrical signals from the pixel circuits of the sensor panel 101. The control circuit 105 is configured to control the radiation detection apparatus 100 as a whole. The wireless communication circuit 106 is configured to perform wireless communication between the radiation detection apparatus 100 and an external apparatus using the antenna 110. "External apparatus" refers to an apparatus outside the radiation detection apparatus 100. The battery 108 supplies operating power to each constituent element of the radiation detection apparatus 100. Instead, the wireless communication circuit 106 and the connector 107 may be mounted on the printed circuit board 103, and the wireless communication circuit 106 and the connector 107 may be mounted on another different printed circuit board.

In realizing the positional relationships between the antenna 110, the radio wave transmission regions 113 and 114, and the reflective member 115 described later, the printed circuit board 103 and the battery 108 need not be located in the vicinity thereof. For example, as illustrated in FIG. 1C, the printed circuit board 103 and the battery 108 may be provided on the side opposite from the antenna element in plan view relative to the sensor support plate 102.

The antenna 110 is constituted by an antenna element 110a and a conductive plate 110b. The conductive plate 110b is mounted to the sensor support plate 102. The conductive plate 110b is located between the antenna element 110a and the sensor support plate 102. The antenna 110 and the connector 107 are connected to each other by the coaxial cable 109. The coaxial cable 109 functions as a power supply line for the antenna 110. The coaxial cable 109 has a first conductor and a second conductor that are electrically separated from each other. For example, the coaxial cable 109 has an inner conductor (also called a "core wire") and an outer conductor (also called an "outer covering"), and these conductors are electrically separated from each other. Two members being "electrically separated from each other" may mean that the members do not constitute the same node in an equivalent circuit diagram. On the other hand, two members being "electrically connected to each other" may mean that the members constitute the same node in an equivalent circuit diagram.

Electrical signals corresponding to data signals to be transmitted wirelessly are supplied from the wireless communication circuit 106 to the antenna element 110a through the inner conductors of the connector 107 and the coaxial cable 109. Ground potential is supplied from the wireless communication circuit 106 to the conductive plate 110b through the outer conductors of the connector 107 and the coaxial cable 109. The antenna element 110a radiates radio waves according to the supplied electrical signal. For example, the antenna element 110a may be used to wirelessly transmit image signals generated by the radiation detection apparatus 100. Furthermore, the antenna element 110a may be used to receive radio waves, including signals from external apparatuses. In this manner, the antenna element 110a is used for wireless communication with external apparatuses. In the examples in FIGS. 1A to 1C, the antenna element 110a and the conductive plate 110b constitute an inverted L-shaped antenna. Alternatively, the antenna 110 may be an inverted F-shaped antenna, a monopole antenna, a dipole antenna, or an antenna having any other configuration.

The antenna element 110a is configured to transmit and receive radio waves at a specific operating frequency. The operating frequency may be a frequency that is suitable for transmission and reception by the antenna element 110a (e.g., high gain). The antenna element 110a may take any frequency within a specific frequency band range as the operating frequency. In this case, this specific frequency band range may be called an "operating frequency band". The antenna element 110a may have a plurality of frequency bands as operating frequency bands.

For example, assume that the antenna element 110a is a dual-band antenna used in wireless communication compliant with wireless LAN (IEEE 802.11a/b/g/n/ac) standards. In this case, the operating frequency band of the antenna element 110a is both the 2.4 GHz and 5 GHz bands. Assume that the antenna element 110a is a single-band antenna used in wireless communication compliant with wireless LAN (IEEE 802.11b/g/n) standards. In this case, the operating frequency band of the antenna element 110a is the 2.4 GHz band. Assume that the antenna element 110a is a single-band antenna used in wireless communication compliant with wireless LAN (IEEE 802.11a/n/ac) standards. In this case, the operating frequency band of the antenna element 110a is the 5 GHz band. Assume that the antenna element 110a is a tri-band antenna used in wireless communication functions compliant with wireless LAN (IEEE 802.11a/b/g/n/ac/ax/be) standards. In this case, the operating frequency bands of the antenna element 110a are the 2.4 GHz, 5 GHz, and 6 GHz bands. However, the operating frequency band of the antenna element 110a may be different from those mentioned above.

Radio waves radiated from the antenna element 110a propagate to the outside of the housing 111 through the radio wave transmission regions 113 and 114. Radio waves from external apparatuses propagate into the interior of the housing 111 through the radio wave transmission regions 113 and 114. Although the radio wave transmission region 113 is described hereinafter, the same descriptions apply to the radio wave transmission region 114 as well. The radio wave transmission region 113 is a region of the housing 111 where the radio wave transmittance is higher than the conductor region surrounding the radio wave transmission region 113. For example, the radio wave transmission region 113 may be formed by removing part of the housing 111 formed from the conductive material. In other words, the radio wave transmission region 113 does not contain a conductive material. The radio wave transmission region 113 includes a part that is at least one-half the width of the wavelength of the operating frequency of the antenna element 110a. For example, if the radio wave transmission region 113 is rectangular in shape, at least the long side thereof is at least one-half the wavelength of the operating frequency of the antenna element 110a. When the antenna element 110a has a plurality of operating frequencies, the radio wave transmission region 113 includes a part that is at least one-half the width of the wavelength of the lowest operating frequency of the antenna element 110a. The antenna element 110a is located closer to the side face 111f than to the side face 111e. Accordingly, the radio wave transmission region 113 is formed in the side face 111e instead of the side face 111f.

The radio wave transmission region 113 may be covered by an insulator cover. This cover may have light-shielding properties to suppress exposure of the sensor panel 101 to outside light. For example, the cover may be formed from a resin. The locations and number of radio wave transmission regions 113 and 114 are not limited to the above examples. The housing 111 may have another radio wave transmission region instead of or in addition to the radio wave transmission region 113 and the radio wave transmission region 114. For example, the housing 111 may have another radio wave transmission region in the side face 111c. In plan view relative to the radio wave transmission region 113 (i.e., when viewed from the y-axis direction), at least part of the antenna element 110a overlaps the radio wave transmission region 113. In the example in FIG. 1B, the entire antenna element 110a overlaps the radio wave transmission region 113 in plan view relative to the radio wave transmission region 113.

Figure 2A:
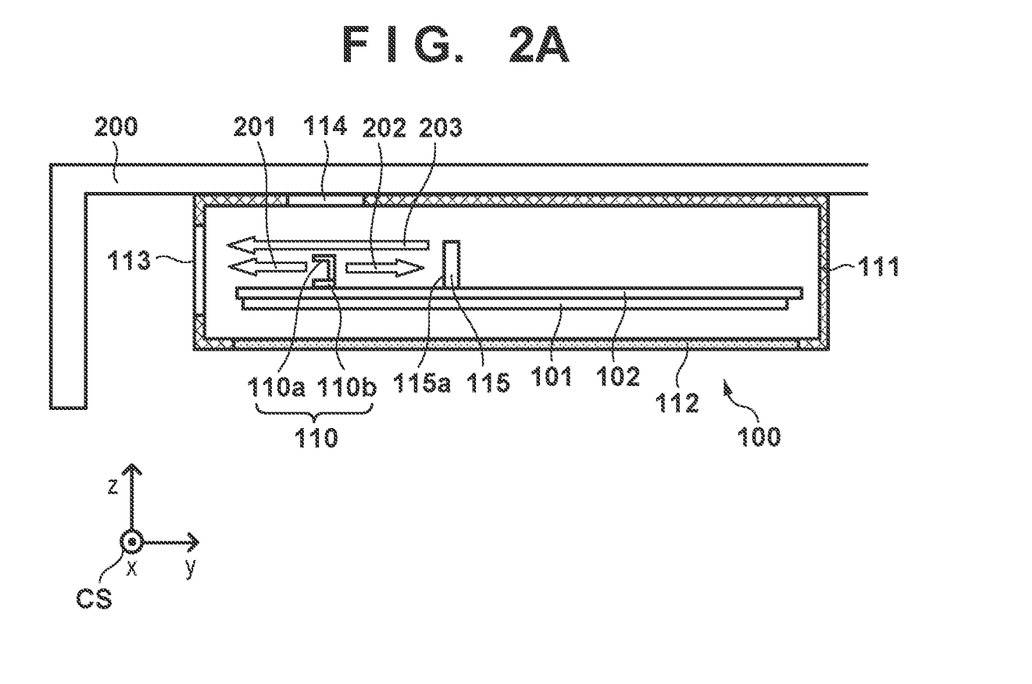
FIGS. 2A and 2B are schematic diagrams illustrating an example configuration of a reflective member according to some embodiments.

The reflective member 115 is on the opposite side from the radio wave transmission region 113 with respect to the antenna element 110a. In other words, the antenna element 110a is located between the reflective member 115 and the radio wave transmission region 113, and is interposed therebetween. Of the plurality of faces of the reflective member 115, the face on the side of the antenna element 110a is called a "reflective face 115a" (FIG. 2A). The reflective member 115 is formed from a material that reflects radio waves, e.g., a conductive material. The reflective member 115 may be formed from a metal such as magnesium, stainless steel, aluminum, copper, iron, or the like. The reflective member 115 may be formed from a resin with metal embedded therein in a mesh-like pattern. The reflective member 115 may be formed from a conductive resin such as carbon-fiber-reinforced plastic (CFRP). The reflective member 115 may be electrically connected to the sensor support plate 102.

In plan view relative to the radio wave transmission region 113 (i.e., when viewed from the y-axis direction), the reflective member 115 may be larger than the antenna element 110a. Specifically, the entire antenna element 110a may overlap the reflective member 115 in plan view relative to the radio wave transmission region 113. The antenna element 110a and the radio wave transmission region 113 are located in the normal direction of the reflective face 115a of the reflective member 115 (i.e., in the y-axis negative direction).

The reflective member 115 is described in detail with reference to FIGS. 2A and 2B. FIG. 2A is a cross-sectional view of the radiation detection apparatus 100 in a plane parallel to the x-y plane and passing through the radio wave transmission regions 113 and 114, the antenna 110, and the reflective member 115. In the following description, a distance between the antenna element 110a and the reflective face 115a in the normal direction of the reflective face 115a is assumed to be L. The distance L is the distance between an end part of the antenna element 110a on the reflective member 115 side and the reflective face 115a, as illustrated in FIG. 1C. The length of the reflective member 115 in the normal direction of the reflective face 115a (also called the thickness of the reflective member 115) is D.

FIG. 2A illustrates the radiation detection apparatus 100 mounted on a frame 200. The radiation detection apparatus 100 may be mounted on such a frame 200 at the time of use. When the frame 200 is constituted by a conductive material, the radio wave transmission region 114 is blocked, and the efficiency of radio wave propagation through the radio wave transmission region 114 is reduced. On the other hand, the radio wave transmission region 113, which is located on the side face of the housing 111, is less likely to be blocked when the radiation detection apparatus 100 is in use. Accordingly, it is important to improve the propagation efficiency of radio waves through the radio wave transmission region 113.

Some radio waves (denoted as "radio waves 201") radiated from the antenna element 110a proceed directly from the antenna element 110a to the radio wave transmission region 113. Some other radio waves (denoted as "radio waves 202") radiated from the antenna element 110a proceed from the antenna element 110a toward the reflective member 115 and reach the reflective face 115a. The reflective face reflects the radio waves 202 as radio waves 203. The radio waves 203 proceed toward the radio wave transmission region 113. According to some embodiments, the reflective member 115 is disposed in a position such that the radio waves 201 and the radio waves 203 strengthen each other. This enables more efficient propagation of radio waves from the antenna element 110a to the outside of the housing 111 compared to a radiation detection apparatus which does not have the reflective member 115.

Specific conditions under which the radio waves 201 and the radio waves 203 strengthen each other are described hereinafter. The operating frequency of the antenna element 110a is represented by f. When the antenna element 110a has a plurality of operating frequencies (e.g., operating frequencies within a specific operating frequency band), f may be any one of the plurality of operating frequencies. For example, f may be the highest of the plurality of operating frequencies. Assume, for example, that the operating frequency band of the antenna element 110a is both the 2.4 GHz and 5 GHz bands. In this case, if the conditions for improving the radio efficiency described below for the 5 GHz operating frequency are satisfied, the radio efficiency can be improved for the 2.4 GHz operating frequency as well.

Assume that $\lambda$ is the wavelength of the operating frequency f. $\lambda$ is calculated as $\lambda=c/f$, using the speed of light c. Because the reflective member 115 is electrically connected to the sensor support plate 102, which has a low impedance, the reflective face 115a acts as a fixed end with respect to the reflection of radio waves. Accordingly, when radio waves are reflected by the reflective face 115a, the phase is inverted. As such, the radio waves 201 and the radio waves 203 strengthen each other most when the distance L between the antenna element 110a and the reflective face 115a is an odd-numbered multiple of $\lambda/4$. If the deviation between the distance L and an odd-numbered multiple of $\lambda/4$ is smaller than $\lambda/8$, the radio waves 201 and the radio waves 203 will strengthen each other.

The shorter the distance L becomes, the more likely it is that the radio waves 203 will concentrate in the radio wave transmission region 113. Therefore, according to some embodiments, the antenna element 110a and the reflective member 115 are disposed such that the distance L is greater than $\lambda/8$ and less than $3\lambda/8$. Furthermore, the distance L may be equal to $\lambda/4$, where the mutual strengthening is strongest in this range.

Other conditions for improving the radio efficiency are described next. A thickness D of the reflective member 115 may be greater than the skin depth of the reflective member 115 with respect to the operating frequency f described above. The skin depth is given by $\sqrt{\{(2\rho)/(2\pi f\mu)\}}$, where $\rho$ is the electrical resistivity of the reflective member 115 and is the magnetic permeability of the reflective member 115. By satisfying such a condition for the thickness D, the reflectance of radio waves at the reflective face 115a is improved, which increases the efficiency of radio waves propagated to the outside of the housing 111.

Other conditions for improving the radio efficiency are described with reference to FIG. 2B. FIG. 2B is a diagram illustrating the reflective face 115a viewed from the front (the y-axis direction). The length of the reflective face 115a in the direction parallel to the incident face 111a (i.e., a direction parallel to the x-y plane) (this can also be called the width of the reflective face 115a) is represented by W. The width W is also the length of the incident face 111a in the x-axis direction. In some embodiments, the width W is greater than $n\lambda/2-\lambda/8$ and less than $n\lambda/2+\lambda/8$, where n is an integer. For example, the width W may be equal to $\lambda$.

Figure 2B:
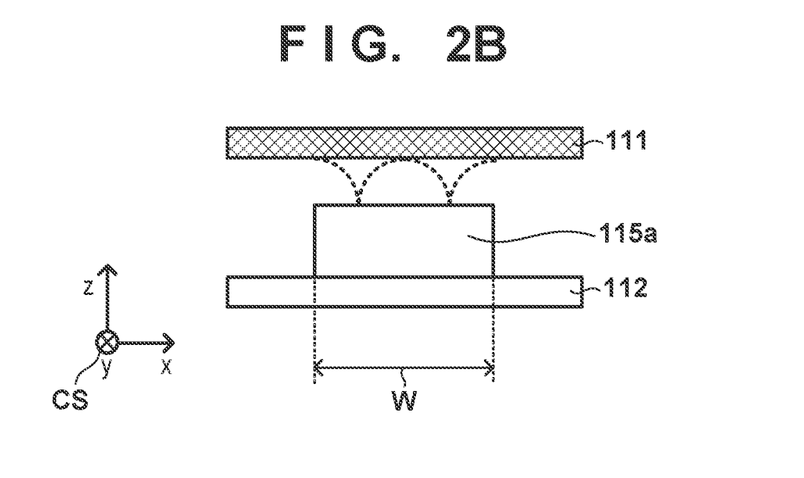

FIG. 2B uses a broken line to indicate an image of an electrical field formed in a gap between the reflective member 115 and the housing 111 when the width W is equal to $\lambda$. In this case, a one-wavelength standing wave is generated in which the electrical field is maximum at both ends of the reflective member 115. This resonance phenomenon results in secondary radiation of radio waves from this gap, which increases the radio emission amount from the radio wave transmission region 113. The resonance phenomenon, in which the electrical field is maximum at both ends of the gap, occurs when the width W is an integral multiple of half the wavelength (i.e., $\lambda/2$). If the discrepancy between the width W and the integral multiple of half the wavelength is smaller than $\lambda/8$, the effect produced by resonance can be obtained. Therefore, by setting the width W to the range described above, the radio emission amount from the radio wave transmission region 113 can be improved.

The reflective member 115 may be disposed such that a distance (i.e., the difference in z-coordinate values) between the center of the radio wave transmission region 113 and the center of the reflective face 115a in a direction parallel to the incident face 111a is small in plan view relative to the radio wave transmission region 113 (i.e., in the y-axis direction). For example, the distance between these centers may be less than $\lambda/2$, or may be zero (i.e., the x-coordinate values of the centers coincide). The shorter the distance between these centers is, the more efficiently radio waves are reflected from the reflective face 115a toward the radio wave transmission region 113.

In the example described above, the antenna 110 (and specifically, the conductive plate 110b thereof) contacts the sensor support plate 102. Instead of this, the antenna 110 may be mounted to the sensor support plate 102 over another member, such as a resin member or the like. In the example described above, the reflective member 115 contacts the sensor support plate 102 and is mounted to the sensor support plate 102. Instead of this, the reflective member 115 may be mounted to the housing 111, or may be mounted to another member. The reflective member 115 may be integrally formed with another member such as the sensor support plate 102 and the housing 111. In the example described above, a gap is present between the housing 111 and the reflective member 115 in the z-axis direction, but the housing 111 and the reflective member 115 may be in contact, with no gap being present.

In the example described above, the reflective member 115 is a single rectangular body. Instead of this, the reflective member 115 need not be a single body, and need not be a rectangular body. Various variations on the reflective member 115 are described with reference to FIGS. 3A to 3F.

Figure 3A:
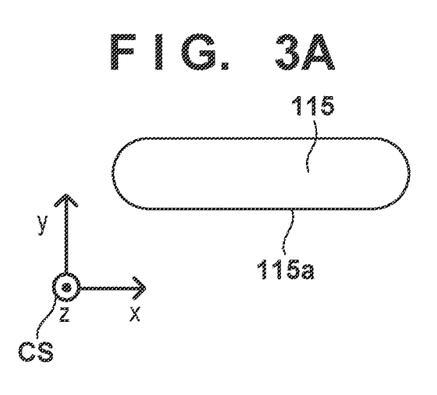
FIGS. 3A to 3F are schematic diagrams illustrating an example configuration of a reflective member according to some embodiments.
Figure 3B:
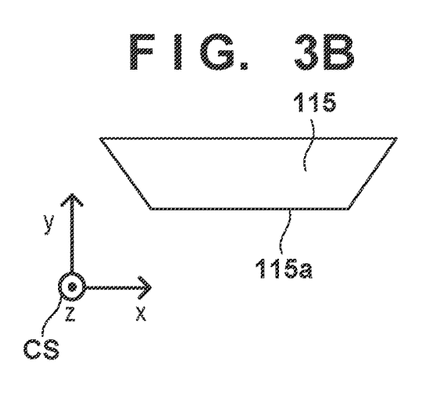
Figure 3C:
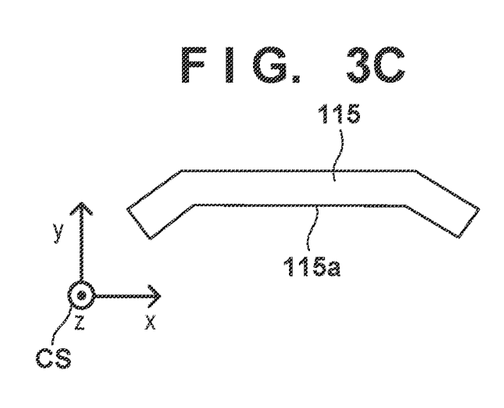

The cross-section of the reflective member 115 in a plane parallel to the x-y plane may be rounded, as illustrated in FIG. 3A, or trapezoidal, as illustrated in FIG. 3B. Additionally, as illustrated in FIG. 3C, the reflective face 115a may have a concave shape. The concave shape may be a connection of planes of different orientations, or may be a curved surface. The reflective face 115a having a concave shape in this manner makes it easier to cause the radio waves 203 reflected by the reflective face 115a to concentrate in the radio wave transmission region 113. The concave shape may be realized by bending both ends of the reflective face 115a, or by bending only one side.

Figure 3D:
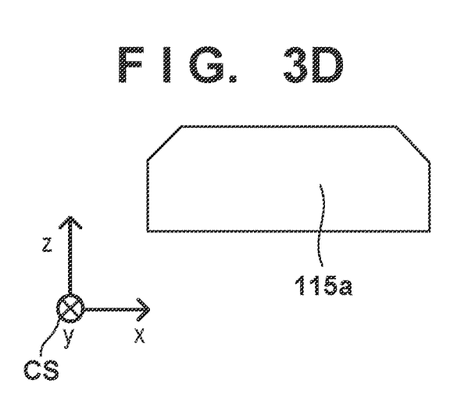

FIG. 3D illustrates a variation on the shape of the reflective face 115a. The reflective face 115a may vary in distance in the z-axis direction (which can also be called the height) depending on the position in the x-axis direction. Changing the height in this manner results in resonance occurring at a plurality of frequencies, which broadens the frequencies at which the radio emission amount is increased.

Figure 3E:
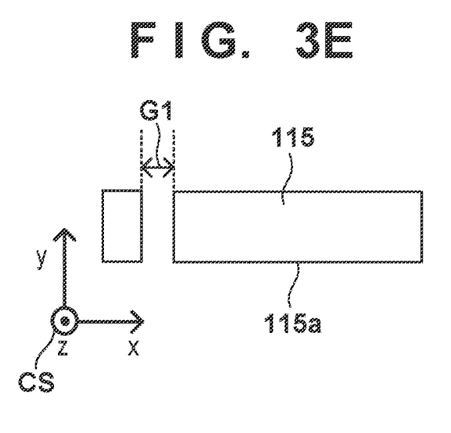

As illustrated in FIG. 3E, the reflective member 115 may be separated into a plurality of parts (two, in the example in the drawing). For example, a gap between the two parts may be used to run the coaxial cable 109. In this case, the distance between two mutually-adjacent parts among the plurality of parts (e.g., a distance G1, in FIG. 3E) may be smaller than $\lambda/2$. By satisfying this condition, a situation where radio waves pass through the gap between the two parts of the reflective member 115 can be suppressed, which improves the radio emission amount from the radio wave transmission region 113.

Figure 3F:
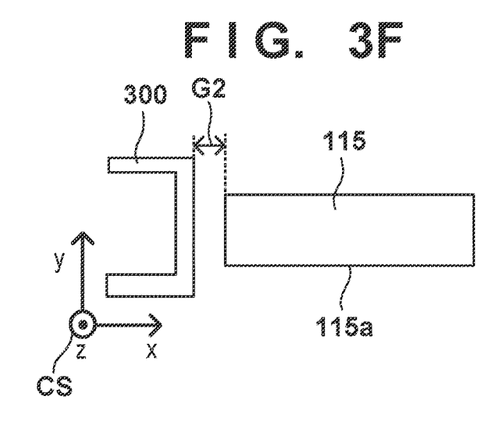

Assume another conductive member 300 is present in the periphery of the reflective member 115, as illustrated in FIG. 3F. The conductive member 300 is provided, for example, to increase the mechanical strength of the radiation detection apparatus 100. The conductive member 300 may be mounted to the face, of the faces of the sensor support plate 102, which is on the same side as the reflective member 115. In this case, a distance G2 between the conductive member 300 and the reflective member 115 may be smaller than $\lambda/2$. By satisfying this condition, a situation where radio waves pass between the conductive member 300 and the reflective member 115 can be suppressed, which improves the radio emission amount from the radio wave transmission region 113.

Numerical Experiments

Figure 4A:
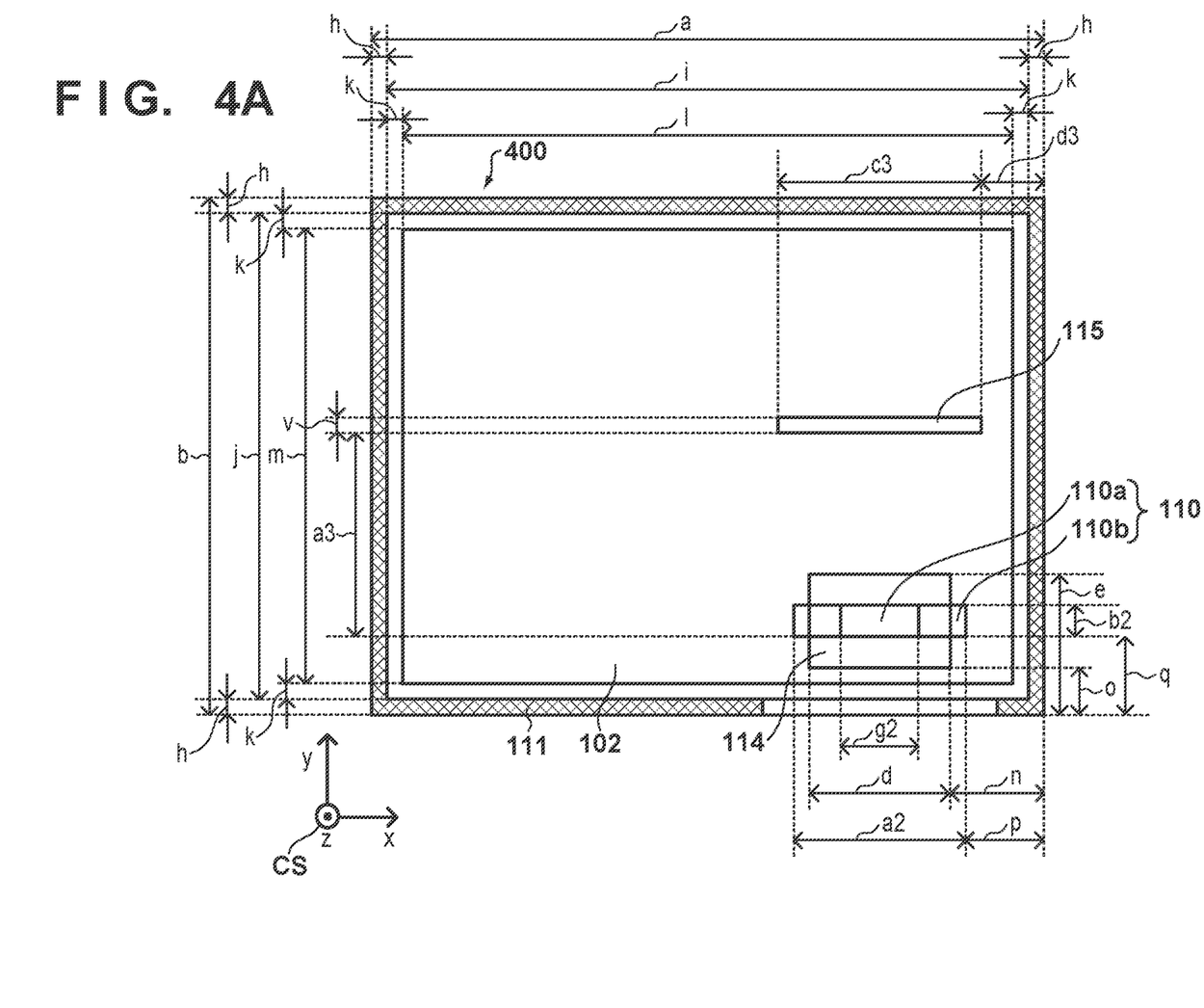
FIGS. 4A and 4B are schematic diagrams illustrating a radiation detection apparatus used in an experiment according to some embodiments.
Figure 4B:
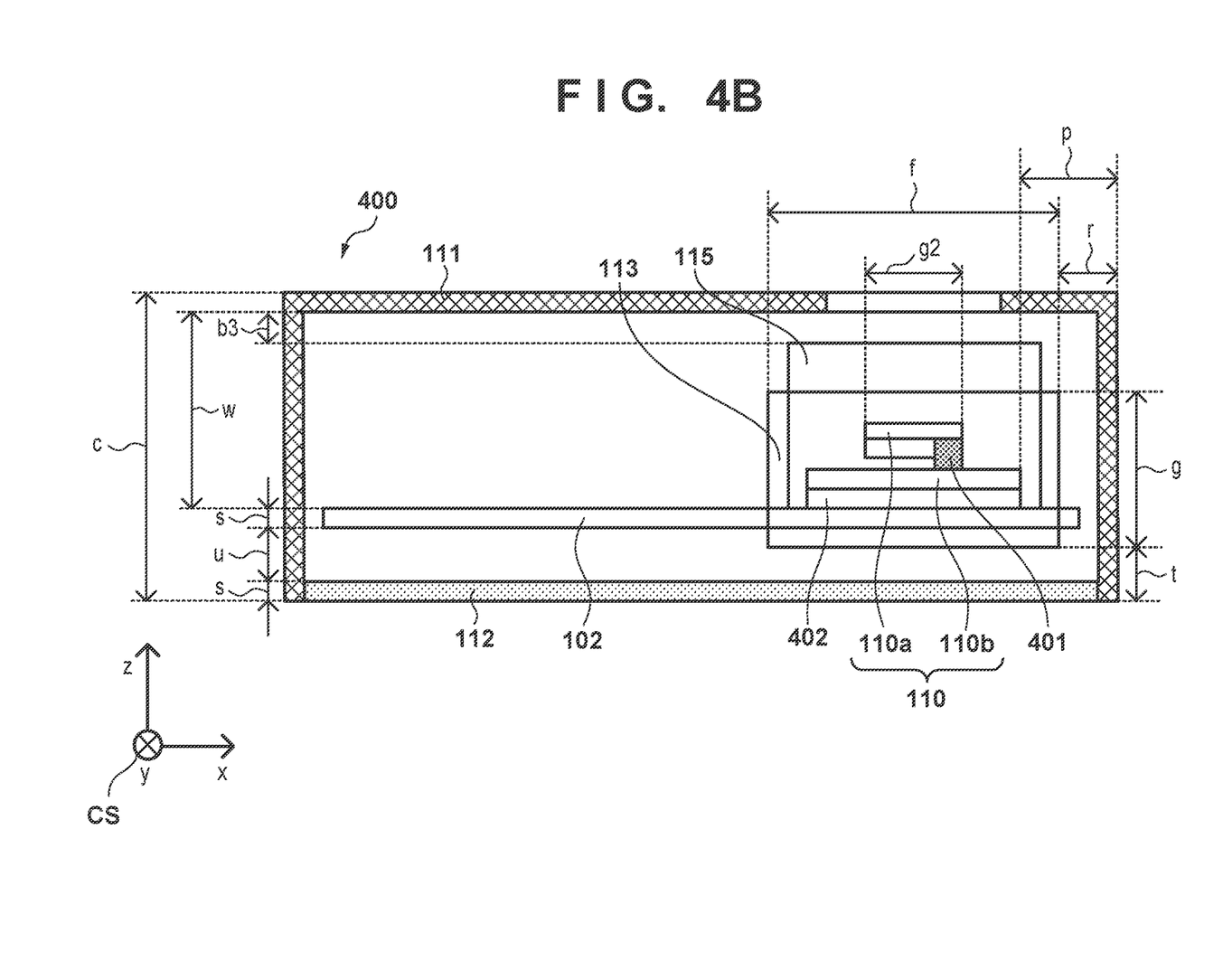

To verify the effects of the radiation detection apparatus 100 described above, numerical experiments were conducted using the electromagnetic field simulator MW-STUDIO manufactured by Computer Simulation Technology (CST). The results are described hereinafter. The configuration of a radiation detection apparatus 400 used in the experiments is described hereinafter with reference to FIGS. 4A and 4B. FIG. 4A is a cross-sectional top view of the radiation detection apparatus 400. FIG. 4B is a cross-sectional side view of the radiation detection apparatus 400. The radiation detection apparatus 400 does not include the constituent elements of the radiation detection apparatus 100 that have little effect on the experiments. Specifically, the radiation detection apparatus 400 includes the antenna element 110a, the conductive plate 110b, the reflective member 115, the sensor support plate 102, and the housing 111, and does not include the other constituent elements of the radiation detection apparatus 100.

The antenna element 110a and the conductive plate 110b are connected by a member 401. A monopole antenna has been used as the antenna 110. Instead of supplying power using the coaxial cable 109, a wave source port was set between the antenna element 110a and the conductive plate 110b. The antenna 110 has been fixed to the sensor support plate 102 using a resin member 402 that simulated double-sided tape. The part 112 of the housing 111 on the incident face side has been a conductive resin member. The radio wave transmission regions 113 and 114 are openings.

Table 1 below shows the lengths of the various parts of the radiation detection apparatus 400 illustrated in FIGS. 4A and 4B.

TABLE 1

| Sign | a | b | c | d | e | f | g | h |
|---|---|---|---|---|---|---|---|---|
| Length (mm) | 460.0 | 384.0 | 15.5 | 40.0 | 20.0 | 58.3 | 5.0 | 6.0 |
| Sign | i | j | k | l | m | n | o | p |
| Length (mm) | 448.0 | 372.0 | 4.0 | 440.0 | 364.0 | 115.0 | 14.3 | 112.3 |
| Sign | q | r | s | t | u | v | w | |
| Length (mm) | 21.4 | 105.9 | 1.5 | 5.0 | 3.0 | 1.5 | 8.3 | |
| Sign | a2 | | b2 | | | | g2 | |
| Length (mm) | 50.0 | | 6.0 | | | | 26.5 | |

Table 2 below shows the electrical properties of the various parts of the radiation detection apparatus 400 illustrated in FIGS. 4A and 4B.

TABLE 2

| Sign | Conductivity (S/m) | Dielectric constant | Relative permeability |
|---|---|---|---|
| 110a | $1.04 \times 10^7$ | 1 | 1 |
| 110b | $1.04 \times 10^7$ | 1 | 1 |
| 401 | — | 2.9 | 1 |
| 102 | $2.27 \times 10^7$ | 1 | 1 |
| 402 | — | 3.7 | 1 |
| 111 | $2.27 \times 10^7$ | 1 | 1 |
| 112 | 8900 | 3 | 1 |
| 115 | $2.27 \times 10^7$ | 1 | 1 |

The parameters to be varied in the simulation were a distance a3 between the antenna element 110a and the reflective face 115a, a distance b3 between the reflective member 115 and the housing 111 in the z-axis direction, a width c3 of the reflective face 115a, and a distance d3 between the reflective member 115 and the housing 111 in the x-axis direction. The effect of increasing the radio emission amount was evaluated using radiation efficiency. The radiation efficiency is determined as the ratio of the power of the radio waves reaching the distant field to the power supplied to the wave source port. The operating frequency of the antenna element 110a was 5.1 GHz.

As described with reference to FIG. 2A, assuming a case where the radio wave transmission region 114 included in the rear face 111b is covered, a numerical experiment was also conducted for a case where the radio wave transmission region 114 is covered by a metal plate. The size of the metal plate has been set to 42 mm×22 mm×1 mm, and the conductivity of the metal plate has been set to $3.56 \times 10^7$ [S/m].

Figure 5A:
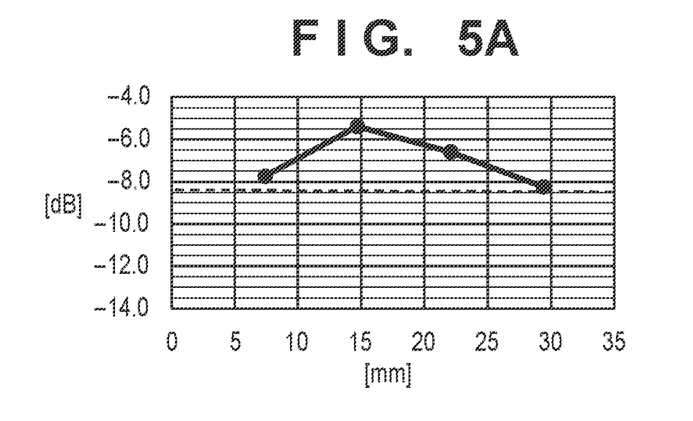
FIGS. 5A to 5H are graphs illustrating experimental results according to some embodiments.
Figure 5B:
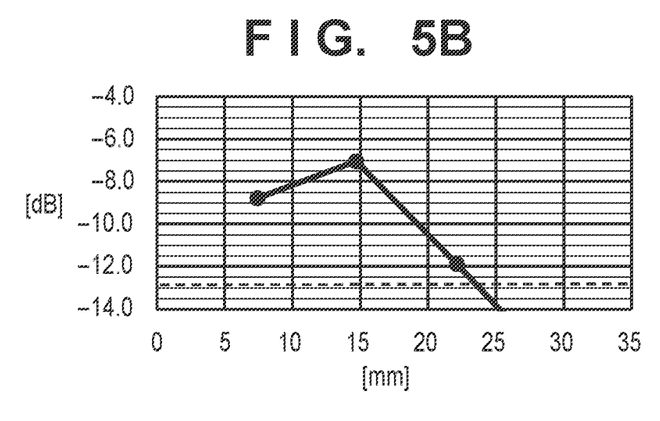

FIGS. 5A and 5B illustrate the radiation efficiency when b3, c3, and d3 are fixed at 1 mm, 58.8 mm, and 105.6 mm, respectively, and a3 is varied. The horizontal axis of the graph represents the distance a3 between the antenna element 110a and the reflective face 115a, and the vertical axis represents the radiation efficiency. FIG. 5A illustrates a case without the metal plate, and FIG. 5B illustrates a case with the metal plate. The dotted line in the drawings represents the value of the radiation efficiency when the reflective member 115 is not provided. Note that b3=1 mm corresponds to a case where the height of the reflective member 115 is 7.3 mm. c3=58.8 mm is the length corresponding to one wavelength of the operating frequency. d3=105.6 mm corresponds to the position when the x coordinate of the center of the radio wave transmission region 113 and the x coordinate of the center of the reflective face 115a coincide.

The results in FIGS. 5A and 5B indicate that the distance a3 between the antenna element 110a and the reflective face 115a is most effective at 14.7 mm, which is ¼ the wavelength of the operating frequency. It can also be seen that the effect is obtained in the range from 7.4 mm, which is ⅛ the wavelength, to 22.1 mm, which is 3λ/8 the wavelength.

Figure 5C:
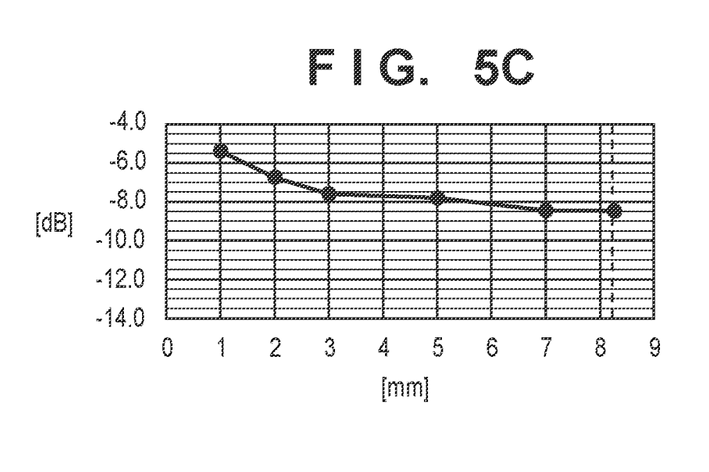
Figure 5D:
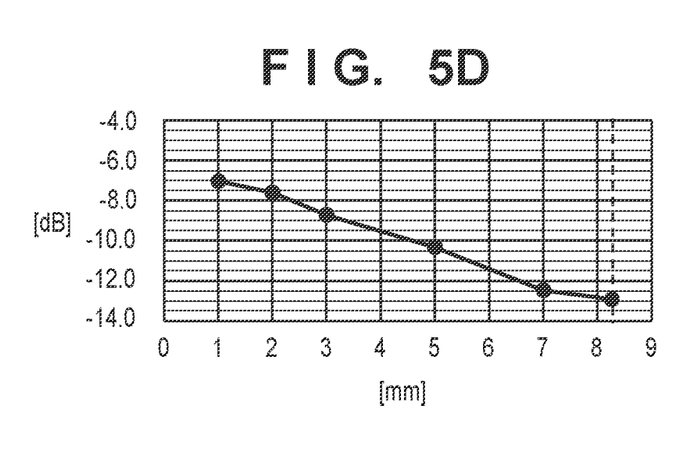

FIGS. 5C and 5D illustrate the radiation efficiency when a3, c3, and d3 are fixed at 14.7 mm, 58.8 mm, and 105.6 mm, respectively, and b3 is varied. The horizontal axis of the graph represents the distance b3 between the reflective member 115 and the housing 111 in the z-axis direction, and the vertical axis represents the radiation efficiency. FIG. 5C illustrates a case without the metal plate, and FIG. 5D illustrates a case with the metal plate. The dotted line in the drawings represents the value of the radiation efficiency when the reflective member 115 is not provided.

The results in FIGS. 5C and 5D indicate that as the distance b3 between the reflective member 115 and the housing 111 in the z-axis direction decreases, the effect increases, and a major effect is achieved particularly when the distance is no greater than 3 mm. In FIG. 5C, a major effect is achieved by setting the gap b3 to be no greater than 36% of the length w, when calculated as a percentage of the length w of 8.3 mm from the sensor support plate 102 to the housing 111.

Figure 5E:
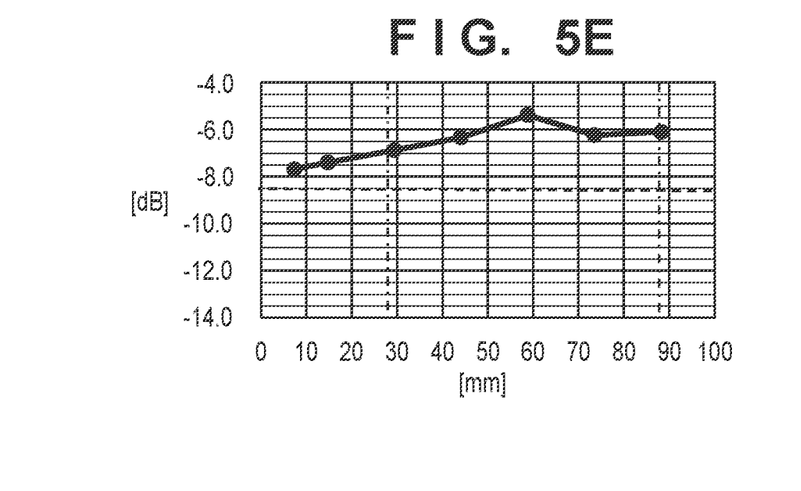
Figure 5F:
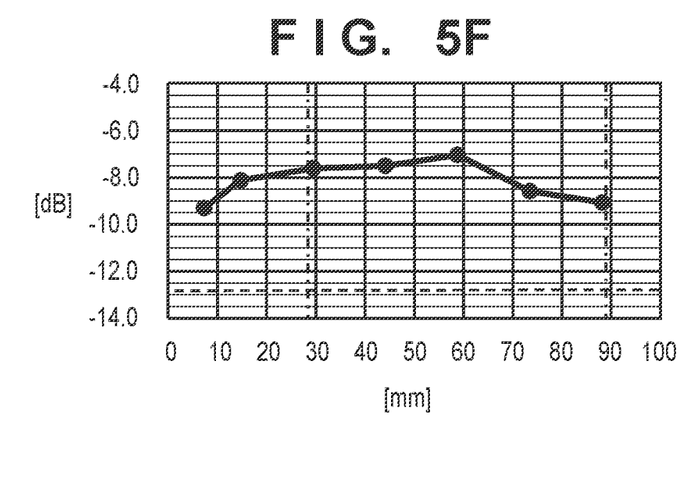

FIGS. 5E and 5F illustrate the radiation efficiency when a3, b3, and d3 are fixed at 14.7 mm, 1 mm, and 105.6 mm, respectively, and c3 is varied. The horizontal axis of the graph represents the width c3 of the reflective face 115a, and the vertical axis represents the radiation efficiency. FIG. 5E illustrates a case without the metal plate, and FIG. 5F illustrates a case with the metal plate. The dotted line in the drawings represents the value of the radiation efficiency when the reflective member 115 is not provided.

The results in FIGS. 5E and 5F indicate that the best effect is obtained when the width c3 of the reflective face 115a is 58.8 mm, which is almost equal to the length f of 58.3 mm. When an electrical field distribution has been output near the reflective member 115 when c3 is 58.8 mm, a standing wave at one wavelength has been observed where the electrical field is maximum at both ends of the reflective member 115. This resonance results in secondary radiation of radio waves from the gap between the reflective member 115 and the housing 111 in the z-axis direction, which increases the radio emission amount from the radio wave transmission region 113. The resonance corresponding to the nadir (peak) of the electrical field at both ends of the reflective member 115, is similarly observed at the position where c3 is λ/3 or λ/2, indicated by the dot-dash lines. The horizontal width c3 of the reflective member 115 achieves an effect when n is an integer and the range is set to be greater than $n\lambda/2-\lambda/8$ and less than $n\lambda/2+\lambda/8$.

Figure 5G:
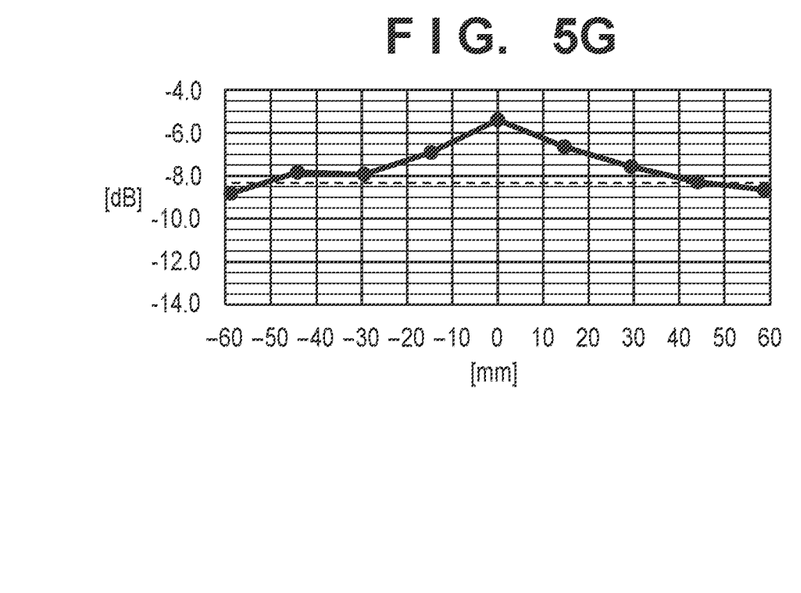
Figure 5H:
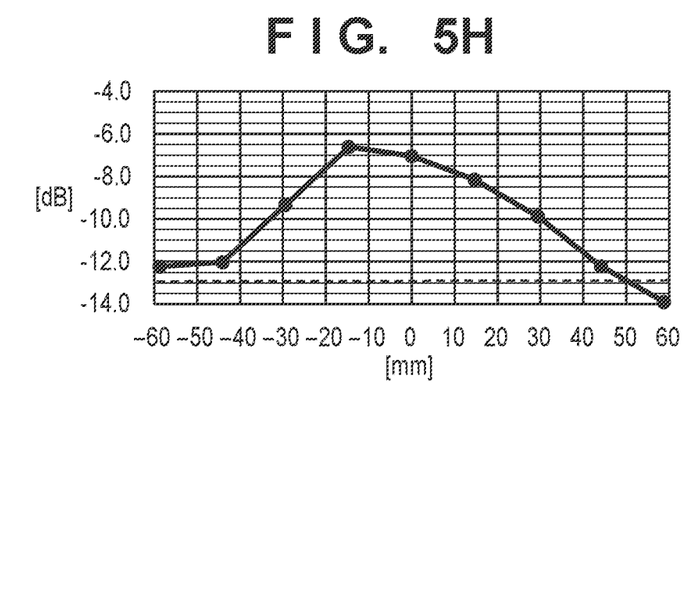

FIGS. 5G and 5H illustrate the radiation efficiency when a3, b3, and c3 are fixed at 14.7 mm, 1 mm, and 58.8 mm, respectively, and d3 is varied. The horizontal axis of the graph represents the difference between the x-coordinate of the center of the radio wave transmission region 113 and the x-coordinate of the center of the reflective face 115a, and the vertical axis represents the radiation efficiency. FIG. 5G illustrates a case without the metal plate, and FIG. 5H illustrates a case with the metal plate. The dotted line in the drawings represents the value of the radiation efficiency when the reflective member 115 is not provided.

The results in FIGS. 5G and 5H indicate that the best effect is achieved when the x-coordinate of the center of the radio wave transmission region 113 coincides with the x-coordinate of the center of the reflective face 115a. The effect is achieved if the difference between the x-coordinates of both centers is less than $\lambda/2=29.4$ mm, which is roughly half of the length f.

OTHER EMBODIMENTS

Figure 6:
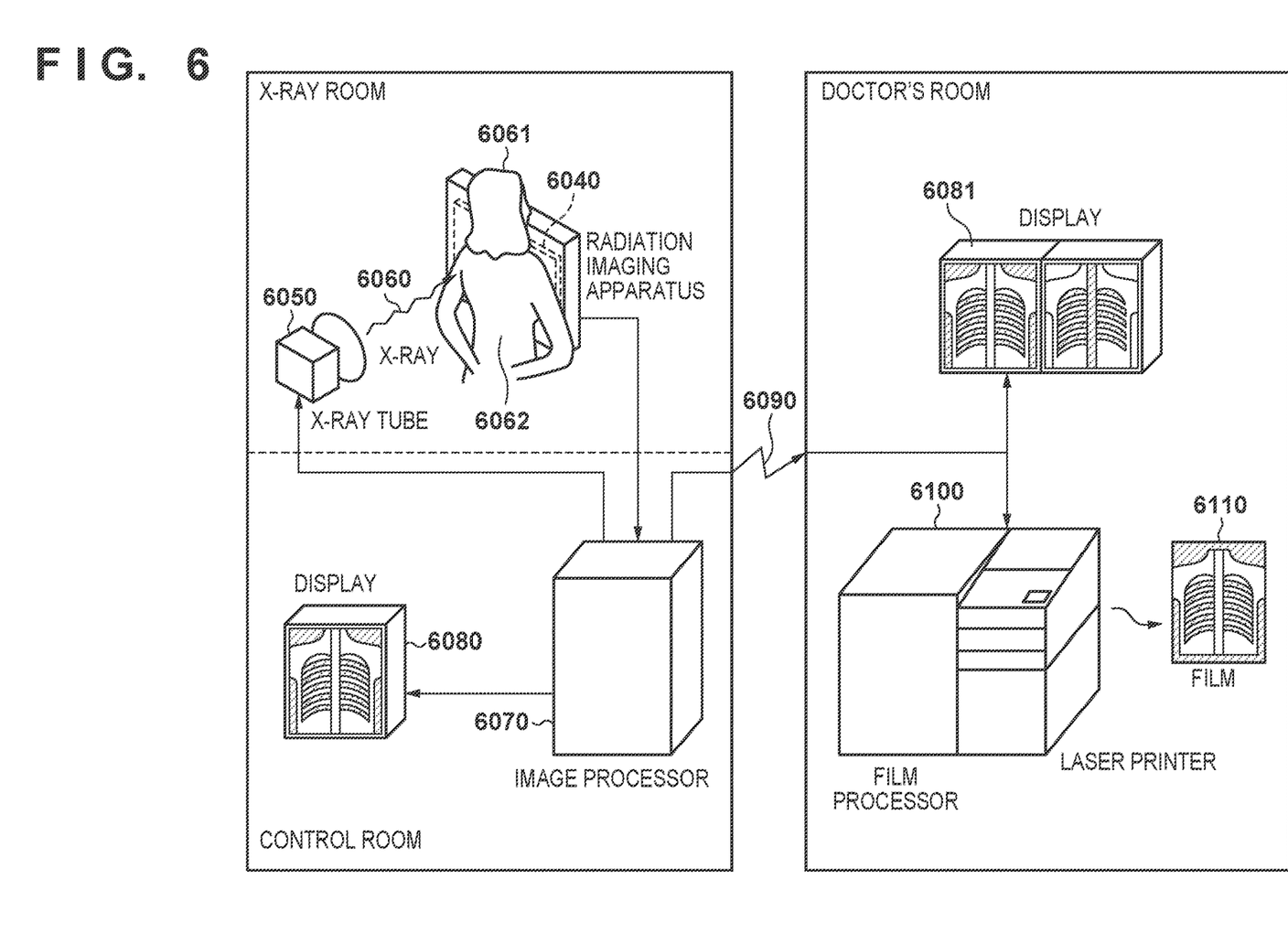
FIG. 6 is a schematic diagram illustrating another embodiment.

FIG. 6 is a diagram illustrating an example of the application of the radiation detection apparatus 100 described above to an X-ray diagnostic system (a radiation detection system). X-rays 6060 as radiation generated by an X-ray tube 6050 (a radiation source) pass through a chest area 6062 of a subject or patient 6061 and enter a detection apparatus 6040. The detection apparatus 6040 may be the radiation detection apparatus 100 described above. The radiation detection apparatus 100 has a scintillator that converts radiation into light. The incident X-rays contain information about the inside of the body of the patient 6061. The scintillator emits light in response to the incident X-rays, and the light is photoelectrically converted to obtain electrical information. This information is converted into a digital signal and undergoes image processing by an image processor 6070, which serves as a signal processing unit, and can then be viewed on a display 6080, which serves as a display unit in a control room. Note that the radiation detection system has at least a radiation detection apparatus and the signal processing unit that processes signals from the radiation detection apparatus.

This information can be transferred to a remote location by a transmission processing unit such as a telephone line 6090, and can be displayed on a display 6081, serving as a display unit in a doctor's room at another location, or saved in a recording unit such as an optical disk or the like, which makes it possible for a physician at the remote location to make a diagnosis. The information can also be recorded onto film 6110, which serves as a recording medium, by a film processor 6100, which serves as the recording unit.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2021-200400, filed Dec. 9, 2021, which is hereby incorporated by reference herein in its entirety.

What is claimed is:

1. A radiation detection apparatus comprising:
a housing having an incident face and a side face;
a reflective member accommodated within the housing, the reflective member having a reflective face which reflects radio waves; and
an antenna element accommodated within the housing,
wherein the side face of the housing includes a conductor region and a transmissive region, the transmissive region having a higher radio wave transmittance than the conductor region, and
the reflective member is disposed in a position at which a first radio wave, which proceeds directly from the antenna element toward the transmissive region, and a second radio wave, which reaches the reflective face from the antenna element and is reflected toward the transmissive region by the reflective face, strengthen each other.

2. The radiation detection apparatus according to claim 1, wherein the antenna element and the transmissive region are positioned in a normal direction of the reflective face of the reflective member.

3. The radiation detection apparatus according to claim 2, wherein a distance between the antenna element and the reflective face in the normal direction of the reflective face is greater than $\lambda/8$ and less than $3\lambda/8$, $\lambda$ representing a wavelength of an operating frequency of the antenna element.

4. The radiation detection apparatus according to claim 1, wherein a length of the reflective face in a direction parallel to the incident face is greater than $n\lambda/2-\lambda/8$ and less than $n\lambda/2+\lambda/8$, n representing an integer and $\lambda$ representing a wavelength of an operating frequency of the antenna element.

5. The radiation detection apparatus according to claim 3, wherein in plan view relative to the transmissive region, a distance between a center of the transmissive region in a direction parallel to the incident face and a center of the reflective face is less than $\lambda/2$.

6. The radiation detection apparatus according to claim 3, wherein a distance between the antenna element and the reflective face in the normal direction of the reflective face is equal to $\lambda/4$.

7. The radiation detection apparatus according to claim 3, wherein a length of the reflective face in a direction parallel to the incident face is equal to $\lambda$.

8. The radiation detection apparatus according to claim 1, wherein a length of the reflective member in the normal direction of the reflective face of the reflective member is greater than a skin depth of the reflective member with respect to an operating frequency of the antenna element.

9. The radiation detection apparatus according to claim 1, wherein the reflective face has a concave shape.

10. The radiation detection apparatus according to claim 3,
wherein the reflective member is separated into a plurality of parts, and a distance between two adjacent parts among the plurality of parts is less than $\lambda/2$.

11. The radiation detection apparatus according to claim 1, further comprising:
a sensor panel configured to convert radiation entering from the incident face into an electrical signal,
wherein the housing further includes a rear face on a side opposite from the incident face, and
the antenna element is positioned between the sensor panel and the rear face.

12. The radiation detection apparatus according to claim 11, further comprising:
 a support plate including a first face to which the sensor panel is mounted and a second face to which the reflective member is mounted; and
 a conductive member mounted to the second face of the support plate,
 wherein a distance between the conductive member and the reflective face of the reflective member is less than $\lambda/2$.

13. The radiation detection apparatus according to claim 12, further comprising:
 a circuit board, mounted to the second face of the support plate, for operating the sensor panel,
 wherein in plan view relative to the second face, the circuit board is provided on a side of the second face that faces the antenna element.

14. The radiation detection apparatus according to claim 1,
 wherein an operating frequency of the antenna element is within a 2.4 GHz band or a 5 GHz band.

15. The radiation detection apparatus according to claim 1,
 wherein the antenna element is configured to wirelessly transmit an image signal generated by the radiation detection apparatus to outside the radiation detection apparatus.

16. A radiation detection apparatus comprising:
 a housing having an incident face and a side face;
 a reflective member accommodated within the housing, the reflective member having a reflective face which reflects radio waves; and
 an antenna element, for generating radio waves, accommodated within the housing, wherein
 the side face of the housing includes a conductor region and a transmissive region, the transmissive region having a higher radio wave transmittance than the conductor region, and
 a radio emission amount from the transmissive region is higher than the radio emission amount when the reflective member is not present.

* * * * *